United States Patent [19]

Hershman

[11] 3,969,398

[45] July 13, 1976

[54] PROCESS FOR PRODUCING N-PHOSPHONOMETHYL GLYCINE

[75] Inventor: Arnold Hershman, Creve Coeur, Mo.

[73] Assignee: Monsanto Company, St. Louis, Mo.

[22] Filed: May 1, 1974

[21] Appl. No.: 465,976

[52] U.S. Cl. .............................................. 260/502.5
[51] Int. Cl.$^2$ ............................................... C07F 9/38
[58] Field of Search ................................... 260/502.5

[56] References Cited
UNITED STATES PATENTS

| | | | |
|---|---|---|---|
| 3,394,172 | 7/1968 | Schieter ........................... | 260/502.5 |
| 3,799,758 | 3/1974 | Franz ................................ | 260/502.5 |
| 3,816,517 | 6/1974 | Krueger et al. ................... | 260/502.5 |

OTHER PUBLICATIONS

Wieland et al., "Chem. Abstracts", vol. 19 (1925), pp. 38, 39.
"Chem. Abstracts", vol. 15 (1921), p. 37.

*Primary Examiner*—Joseph E. Evans
*Attorney, Agent, or Firm*—William T. Black; Donald W. Peterson

[57] ABSTRACT

A process for the production of N-phosphonomethyl glycine by the oxidation of N-phosphonomethylimino diacetic acid utilizing a molecular oxygen-containing gas as the oxidant in the presence of a catalyst consisting essentially of activated carbon. The N-phosphonomethyl glycine produced is useful as a herbicide or plant growth regulant.

12 Claims, No Drawings

PROCESS FOR PRODUCING N-PHOSPHONOMETHYL GLYCINE

The present invention relates to a process for producing N-phosphonomethyl glycine by the oxidation of N-phosphonomethylimino diacetic acid employing activated carbon as the catalyst. More particularly, the present invention is concerned with such oxidation employing a molecular oxygen-containing gas and an activated carbon catalyst.

It is known that N-phosphonomethylimino diacetic acid can be oxidized to N-phosphonomethyl glycine employing many different oxidizing agents. For example, hydrogen peroxide, nitric acid, peroxyacetic and others react with N-phosphonomethylimino diacetic acid at elevated temperatures to produce N-phosphonomethyl glycine. It is also known that N-phosphonomethylimino diacetic acid can be oxidized in aqueous media, e.g. water solutions to N-phosphonomethyl glycine employing a free oxygen-containing gas and a noble metal catalyst such as palladium, platinum, rhodium, etc., either per se or supported on carbon or other supports, at elevated temperatures and in some instances, pressures greater than atmospheric.

It is also known that amino acids can be oxidized to free ammonia and carbon dioxide employing palladium on charcoal or absorbent charcoal as the catalyst [Ann. 439, 196–210 (1924), C.A. 19, 38 (1925)], and [Biochem. Z., 113, 257 (1921); C.A. 15, 1537].

It has surprisingly been discovered that N-phosphonomethylimino diacetic acid can be oxidized to N-phosphonomethyl glycine, preferably in a water solution employing a molecular oxygen-containing gas and activated carbon in a form and quantity sufficient to catalyze the oxidation of the imino diacetic acid.

In accordance with one embodiment of this invention, the N-phosphonomethylimino diacetic acid is dissolved in water and this solution contacted with a molecular oxygen-containing gas in the presence of activated carbon, while heating the mixture to a temperature sufficiently elevated to cause said oxygen and said imino diacetic acid to react to produce N-phosphonomethyl glycine.

It is believed that the reaction takes place in accordance with the following equaltion:

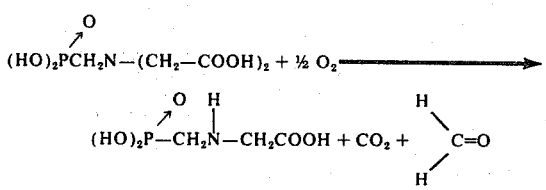

The temperature employed in carrying out the process of this invention should be sufficient to initiate the reaction and to sustain the reaction once intitiated. Temperatures of from about 25°C. to 150°C. or even higher are usually satisfactory. As those skilled in the art would realize, at lower temperatures the rate of reaction is undesirably slow and, therefore, temperatures of at least 75°C. are preferred and even more preferred are temperatures in the range of about 90°C. to 150°C. It is, of course, realized that at temperatures above about 100°C. that pressure will have to be maintained on the system to maintain a liquid phase.

The pressure at which the process of this invention is conducted can vary over wide ranges. Thus, the pressure of the molecular oxygen-containing gas can be as low as 0.5 Kg/cm$^2$ to 200 or more Kg/cm$^2$. It is preferred for convenience to conduct the process of this invention at a total pressure of from 0.5 Kg/cm$^2$ to 200 Kg/cm$^2$. It is even more preferred to conduct the process of this invention at pressures of from 1 Kg/cm$^2$ to 7 Kg/cm$^2$.

The manner in which the aqueous solution of the imino diacetic acid is contacted with the molecular oxygen-containing gas and activated carbon can vary greatly. For example, the imino diacetic acid solution can be placed in a closed container with some free space containing molecular oxygen and shaken vigorously or agitated by stirring or the molecular oxygen-containing gas can be bubbled through said solution containing activated carbon either through a straight tube or a tube with a fritted diffuser attached thereto. The contacting can also be accomplished in a tubular continuous reactor packed with activated carbon. Thus, the process of this invention only requires actively contacting the molecular oxygen-containing gas with the aqueous solution of said N-phosphonomethylimino diacetic acid containing said activated carbon catalyst. As those skilled in the art would realize, merely allowing a water solution of said imino diacetic acid containing said activated carbon to stand in contact with air under proper conditions would produce some of the desired product; however, the amount so produced would be small.

In conducting the process of this invention it is preferred to employ approximately saturated solutions of the N-phosphonomethylimino diacetic acid in water at the temperature of reaction for ease of reaction and ease of recovery of the product, N-phosphonomethyl glycine, i.e., from about 1% by weight at 25°C., about 4% by weight at 95°C. and about 10% by weight at 150°C. It is, of course, possible to employ very dilute, i.e., 0.1% by weight of N-phosphonomethylimino diacetic acid in water; however, this results in a more difficult product recovery procedure. It is also possible to employ supersaturated solutions; however, the use of such solutions is usually not as desirable since the starting material could precipitate out during the reaction, thereby rendering the reaction process more difficult to conduct and separation of the product more difficult.

The amount of the molecular oxygen-containing gas employed can vary over wide ranges. It is, of course, obvious to those skilled in the art that the best yields of the N-phosphonomethyl glycine are produced when at least stoichiometric amounts of oxygen are employed. In most instances for ease of reaction and best yields of the final product, N-phosphonomethyl glycine, the amount of oxygen employed would ordinarily be at least ½ moles of oxygen for each mole of N-phosphonomethylimino diacetic acid employed. In actual practice, the amount of oxygen employed will be from ½ to 1 or more moles for each mole of the N-phosphonomethylimino diacetic acid employed since the efficiency of the oxygen utilization is usually less than 100%.

By the term "molecular oxygen-containing gas", as employed herein, is meant any gaseous mixture containing molecular oxygen with one or more diluents which are non-reactive with the oxygen or with the reactant or product under the conditions of reaction. Examples of such gases are air, oxygen, oxygen diluted with helium, argon, nitrogen, or other inert gas, oxygen-hydrocarbon mixtures and the like. It is preferred to employ gases containing 20 or more percent by weight molecular oxygen and even more preferred to employ gases containing 90 or more percent by weight molecular oxygen. It is, of course, obvious to those of ordinary skill in the art that when molecular oxygen-containing gases containing other inert gases are employed, the pressures should be increased to maintain adequate partial pressures of oxygen in the system to maintain a sufficient rate of reaction.

The activated carbon catalysts employed in the process of this invention are well known in the art and are available under a large number of trade names. These activated carbons are characterized by high adsorptive capacity for gases, vapors and colloidal solids and relatively high specific surface areas. Carbon, char or charcoal is produced by destructive distillation of wood, peat, lignite, nut shells, bones, vegetable or other natural or synthetic carbonaceous matter, but must usually be "activated" develop adsorptive power. Activation is usually achieved by heating to high temperatures (800°–900°C.) with steam or with carbon dioxide, which brings about a porous particle structure and increased specific surface area. In some cases hygroscopic substances, such as zinc chloride and/or phosphoric acid or sodium sulfate, are added prior to the destructive distillation or activation, to increase adsorptive capacity. The carbon content of active carbons ranges from about 10% for bone charcoal to about 98% for some wood chars and nearly 100% for activated carbons derived from organic polymers. The non-carbonaceous matter in activated charcoal will vary depending on precursor origin and/or activation procedure. For example, inorganic "ash" components containing aluminum and silicon are oftentimes present in large amounts accompanied by certain alkali metals and alkaline earths. The latter grouping influences the acidity-basicity characteristics of the activated carbon. Other inorganic constituents found in many activated carbons include iron and titanium. Depending on raw material origin and activation procedure, large amounts of oxygen can be present alongwith lesser amounts of hydrogen, nitrogen and sulfur. Oxygen content also influences activated carbon acidity-basicity.

The specific surface area of activated carbons, measured by the BET (Brunauer-Emmett-Teller) method using $N_2$, can range from 100 to nearly 2000 $m^2/g$. The packed bulk density of activated carbons will depend on the form (powder vs. particulate) and also on the measuring technique employed. Measured values less than 0.15 g/cc and as high or about 0.6 g/cc for powders have been recorded. Particle or skeletal density, determined by mercury intrusion at atmospheric pressure, ranges from about 0.2 g/cc to about 0.53 g/cc on the same samples. Of course, density values on either side of the ranges are possible and it is understood that the values cited are for illustrative purposes and should not be construed as limiting the scope of the present invention.

The specific surface area of the activated carbon employed in the process of this invention can be from 100 to 2000 square meters per gram. It is preferred to employ activated carbons having a specific surface area of from 400 to 1600 square meters per gram.

The amount of granular or powdered activated carbon employed in the process of this invention can range from 0.5 to 100 or more parts by weight for every 100 parts by weight of the N-phosphonomethylimino diacetic acid employed. For the powdered activated carbons, it is preferred to employ from 5 to 20 parts by weight of activated carbon for each 100 parts by weight of the N-phosphonomethylimino diacetic acid. For the activated carbons in granular forms, it is preferred to employ 10 to 75 parts by weight per 100 parts by weight of N-phosphonomethylimino diacetic acid and even more preferred from 20 to 60 parts by weight. It is, of course, obvious that in a tubular type reactor, hereinbefore mentioned, weight ratios of activated carbon to reactants can vary over even greater ranges than herein set forth.

The activated carbons employed in the process of this invention can be in the form of powders or granules.

In the powder form the activated carbons consist largely of material having a particle size finer than 325 mesh (about 45 microns or less in diameter)—although some larger particles may also be present. Particles as small as one micron have been observed by scanning electron microscopy. In the granular form, the particle size range can vary considerably. Particle sizes of 4 × 10 mesh, 8 × 30 mesh and 20 × 30 mesh are all available commercially and can be used. Mesh sizes given herein are those of the U.S. Standard Sieve Series.

The following is a listing of some of the activated carbons which are useful in the process of this invention. This listing is by way of example and is not an exhaustive listing. These activated carbons are for example:

| Trade Name | Sold by |
| --- | --- |
| Darco G-60 Spec. | ICI-America Wilmington, Delaware |
| Darco X | ICI-America Wilmington, Delaware |
| Norit SG Extra | Amer. Norit Co., Inc. Jacksonville, Fla. |
| Norit EN⁴ | '' |
| Norit EXW | '' |
| Norit A | '' |
| Norit Ultra-C | '' |
| Norit ACX | '' |
| XZ | Barnebey-Cheney Columbus, Ohio |
| NW | '' |
| JV | '' |
| Bl. Pulv. | Pittsburgh Activated Carbon Div. of Calgon Corporation Pittsburgh, Pa. |
| PWA Pulv. | '' |
| PCB fines | '' |
| P-100 | No. Amer. Carbon, Inc. Columbus, Ohio |
| Nuchar CN | Westvaco Corporation Carbon Department Covington, Va. |
| Nuchar C-1000N | '' |
| Nuchar C-190A | '' |
| Nuchar C-115A | '' |
| Code 1551 | Baker and Adamson Division of Allied |
| RB-111 | Amer. Norit Co., Inc. Jacksonville, Fla. |
| Norit 4 × 14 mesh | '' |
| GI-9615 | Barnebey-Cheney Columbus, Ohio |
| VG-8408 | '' |
| VG-8590 | '' |
| NB-9377 | '' |
| Grade 235 | Witco Chemical Corp. Activated Carbon Div. New York, New York |
| Grade 337 | '' |
| Grade 517 | '' |
| Grade 256 | '' |
| Columbia SXAC | Union Carbide New York, New York |

The following table gives the properties of a number of common activated carbons in powder form.

POWDERS

| Trade Name | Specific Surface Area (BET) m²/g | Pore Volume cc/g | Density g/cc | pH Water Solution |
|---|---|---|---|---|
| Darco G-60 | 1144 | 2.819 | .310 | 7.5 |
| Darco X | 296 | 1.555 | .440 | 5.0 |
| Norit SG Extra | 820 | 1.669 | .431 | 6.9 |
| Norit EXW | 1082 | 2.205 | .350 | 6.6 |
| Norit Ultra C | 1076 | 2.206 | .354 | 10.0 |
| Norit A | 900 | | .384 | 9.0 |
| Norit ACX | 1360 | | | 2.4 |
| Norit EN'* | 551–900 | | .401 | 7.0 |
| YZ | 1136 | 1.402 | .561 | 8.4 |
| NW | 662 | 1.405 | .482 | 11.4 |
| JV | 743 | 1.599 | .498 | 2.8 |
| Black-pulverized | 972 | 1.600 | .551 | 8.9 |
| PWA-pulverized | 898 | 1.641 | .520 | 8.2 |
| PCB-fines | 1010 | 1.502 | — | 10.1 |
| P-100 | 1394 | 2.500 | .383 | 2.5 |
| Nuchar CN | 963 | 4.537 | .178 | 7.1 |
| Nuchar C-1000N | 986 | 4.918 | .147 | 6.2 |
| Nuchar C-190A | 796 | 4.211 | .222 | 5.3 |
| Nuchar C-115A | 815 | 3.877 | .251 | 5.6 |
| Code 1551 | 458 | 2.310 | — | 3.4 |

Norit EN'* = Purchased from Fisher Scientific Company, Fairlawn, New Jersey.

The following list gives properties of some granular activated carbons.

| Trade Name | Mesh | Specific Surface Area m²/g | pH | Particle Density g/cc |
|---|---|---|---|---|
| Norit RB 111 | 4 × 14 | 797 | 9.2 | .655 |
| Norit 4 × 14 mesh | 4 × 14 | 615 | 10.5 | .530 |
| Gl 9615 | 8 × 14 | 1723 | 11.2 | .650 |
| VG-8408 | 6 × 10 | 670 | 9.2 | .837 |
| NB-9377 | 4 × 10 | 610 | 10.5 | .619 |
| Grade 235 | 4 × 10 | 1046 | 9.8 | .926 |
| Grade 235 | 8 × 30 | | | .918 |
| Grade 337 | 8 × 16 | | | |
| Grade 337 | 10 × 20 | | | |
| Grade 517 | 8 × 30 | | | |
| Grade 517 | 18 × 40 | | | |
| Grade 256 | 4 × 10 | 1130 | 9.9 | .788 |
| Columbia SXAC | 6 × 8 | 1245 | 7.1 | .747 |

The starting material employed in the process of this invention is N-phosphonomethylimino diacetic acid and can be produced by the reaction of imino diacetic acid with formaldehyde and phosphorous acid in the presence of hydrochloric acid.

As is apparent from the experiments, the form of the activated carbon, its pH and its surface area, all affect the rate of reaction of the N-substituted imino diacetic acid with oxygen in the process of this invention. The experiments indicate that when the pH of the activated carbon is above about 6.0 the reaction rate is faster than when the pH is below 4.0.

The following examples are representative and illustrate the invention process. All parts, percentages and proportions are by weight unless otherwise indicated.

EXAMPLE 1

A series of runs were made to oxidize N-phosphonomethylimino diacetic acid to N-phosphonomethyl glycine. This series was conducted in a low pressure apparatus consisting of a Parr shaker to provide agitation. The 500 ml. bottle was fitted with a heating mantle and shield and rubber stopper fitted with an entry tube and connected to a manifold system amenable to charging and discharging oxygen from the reactor. Table I gives the results of these experiments. In these experiments, 0.5 grams (g.) of activated carbon, 4.0 g. of N-phosphonomethylimino diacetic acid and 100 g. of distilled water were employed. The N-phosphonomethylimino diacetic acid, water and activated carbon were charged into the bottle and heated to 95°C. on a hot plate and the heating shield heated to 90°C. The bottle was sealed, placed in the shield and alternately pressurized and depressurized several times with oxygen gas at 3.1 Kg/cm² to remove the air. The reactions were all conducted at 3.1 Kg/cm² with discharge and repressurization to ensure sufficient oxygen being present. After the reaction was terminated, the activated carbon was filtered off and the filtrate evaporated under reduced pressure which yielded a solid product. The solid product was analyzed by nuclear magnetic resonance spectral analysis (NMR) and identified as N-phosphonomethyl glycine having a melting point of 230°C. with decomposition.

TABLE I

| Experiment No. | Activated Carbon Employed | Reaction Temp. °C. | Reaction Time (hours) | Final Product Mol % Starting Material | Final Product Mol % N-phosphono-methyl glycine |
|---|---|---|---|---|---|
| 1 | SXAC 325 Mesh | 90–96 | 3.0 | 0.00 | 100 |
| 2 | Neutral Nuchar | 90–95 | 3.0 | 41.86 | 58.14 |
| 3 | Norit "A" | 90–96 | 2.0 | 0.00 | 100 |
| 4 | DARCO G60 | 91–97 | 3.0 | 72.97 | 27.03 |
| 5 | Norit ACX | 90–95 | 3.0 | 75.00 | 25.06 |
| 6 | Activated Coconut Carbon 50–200 Mesh | 90–95 | 3.0 | 48.48 | 51.55 |

In Example 1 when lampblack or graphite were substituted for activated carbon, no reaction took place.

EXAMPLE 2

In this series of experiments on the oxidation of N-phosphonomethylimino diacetic acid to N-phosphonomethyl glycine, the apparatus employed was the same as in Example 1. The experiments were designed to determine if the activated carbon catalyst could be re-used with a small amount of added makeup catalyst to simulate catalyst losses in recycling and/or catalyst inactivation. The data from these experiments is shown in Table II. The time of reaction was 2.0 hours and the reacton pressure 3.1 Kg/cm² in each case. In experiment 13 and 14, deionized water was employed, in all others ordinary tap water was used. In each experiment, the amount of water employed was approximately 100 grams.

TABLE II

| Experiment No. | Catalyst Norit EN[4]* | N-phosphonomethyl-imino diacetic acid Weight | Reaction Temp. °C. | N-phosphonomethyl glycine Yield (%) |
|---|---|---|---|---|
| 7 | 0.5 g. | 4.0 g. | 86–93 | 93.11 |
| 8 | Catalyst from 7 + 0.150 g. | 4.0 g. | 90–95 | 100.00 |
| 9 | 0.623 | 5.0 g. | 90–99 | 94.00 |
| 10 | Catalyst from 9 + 0.1875 g. | 5.0 g. | 90–95 | 87.38 |
| 11 | 0.5625 g. | 4.5 g. | 90–95 | 92.34 |
| 12 | Catalyst from 11 + 0.1687 g. | 4.5 g. | 90–95 | 100.00 |
| 13 | 0.5 g. | 4.0 g. | 90–93 | 94.24 |
| 14 | Catalyst from 13 + 0.0504 g. | 4.0 g. | 90–96 | 83.59 |
| 15 | 0.5 g. | 4.0 g. | 92–93 | 93.21 |
| 16 | Catalyst from 15 + 0.1504 g. | 4.0 g. | 90–96 | 93.03 |
| 17 | 0.5 g. | 4.0 g. | 93–95 | 93.11 |
| 18 | Catalyst from 17 + 0.1502 g. | 4.0 g. | 92–95 | 100.00 |
| 19 | Catalyst from 18 + 0.0751 g. | 4.0 g. | 93–96 | 100.00 |
| 20 | Catalyst from 19 + 0.07573 g. | 4.0 g. | 90–94 | 100.00 |
| 21 | 0.5625 g. | 4.5 g. | 90–95 | 92.34 |
| 22 | Catalyst from 21 + 0.1687 g. | 4.5 g. | 90–96 | 100.00 |
| 23 | Catalyst from 22 + 0.0846 g. | 4.5 g. | 91–99 | 100.00 |

Catalyst Norit EN[4]* = purchased from Fisher Scientific Company, Fairlawn, New Jersey.

EXAMPLE 3

The apparatus employed was the same as in Example 1. The weight of the original catalyst was 0.5 g., and recycled as indicated in Table III. In each experiment, 4 g. of N-phosphonomethylimino diacetic acid dissolved in 100 ml. of distilled water was employed. The yield of N-phosphonomethyl glycine was determined by nuclear magnetic resonance spectral analysis. The results are shown in Table III.

TABLE III

| Experiment Number | Catalyst | Reaction Temp °C. | Reaction Time (hrs.) | % of N-phosphono-methyl glycine |
|---|---|---|---|---|
| 24 | SXAC 325 mesh | 90–96 | 3.0 | 100 |
| 25 | From Expt. No. 24 | 92–96 | 3.0 | 88.37 |
| 26 | Norit EN[4] | 90–96 | 2.0 | 100 |
| 27 | From Expt. No. 26 | 90–95 | 2.0 | 85.72 |
| 28 | From Expt. No. 27 | 90–95 | 2.0 | 70.71 |

EXAMPLE 4

In this series of experiments, a 300 milliliter magnetically-stirred autoclave constructed of Hastelloy C was employed. The system was equipped to discharge gas at a controllable rate by means of metering valve. The flow of oxygen was controlled by pressure and discharge rate.

The procedure employed was as follows. The water (about 100 g.), activated carbon, and N-phosphonomethylimino diacetic acid was charged to the clave and a slow flow of oxygen was intitiated while the clave was being sealed and heated. Upon attaining a temperature of 90°C., the pressure was increased to 3.1 Kg/cm². Samples were withdrawn every ½ hour. After the reaction was terminated, the carbon was filtered off, the reaction mixtures evaporated and the solid dried in vacuo. Analysis of the product, N-phosphonomethyl glycine, was by NMR. The results of this series of experiments are given in Table IV. In this experiments the N-phosphonomethylimino diacetic acid, employed as a starting material, had been recrystallized from water. The oxygen flow rate was maintained at 9.5 cc. per minute with venting to maintain the pressure at 3.1 Kg/cm².

In the experiments where air or other molecular oxygen-containing gas is substituted for oxygen, the reaction proceeds in the same fashion to produce N-phosphonomethyl glycine.

TABLE IV

| Experiment No. | Wt. Norit EN[4] | Weight (g)- N-phosphonomethyl-imino diacetic acid | Reaction Temp °C | Reaction Time (hrs.) | N-phosphonomethyl glycine Yield (%) |
|---|---|---|---|---|---|
| 29 | 0.5 g. | 4.0 | 96.5–100 | 1.5 | 100.00 |
| 30 | Catalyst from 29 | 4.0 | 96.0–98.5 | 1.5 | 96.11 |
| 31 | Catalyst from 30 | 4.0 | 97.5–98.5 | 1.5 | 90.48 |
| 32 | Catalyst from 31 | 4.0 | 94.5–97.0 | 1.5 | 74.32 |
| 33 | 0.5625 g. | 4.5 | 96–99.5 | 1.33 | 100.00 |
| 34 | Catalyst from 33 + 0.1688 g. | 4.5 | 96.5–99.5 | 1.25 | 100.00 |

TABLE IV-continued

| Experiment No. | Wt. Norit EN[4] | Weight (g). N-phosphonomethyl-imino diacetic acid | Reaction Temp °C | Reaction Time (hrs.) | N-phosphonomethyl glycine Yield (%) |
|---|---|---|---|---|---|
| 35 | 34 + 0.0846 g. Catalyst from | 4.5 | 98–99.5 | 1.33 | 100.00 |
| 36 | 35 + 0.0844 g. Catalyst from | 4.5 | 98.5–99.5 | 1.25 | 100.00 |
| 37 | 36 + 0.0845 g. 0.5625 g. of | 4.5 | 97.5–99.5 | 1.25 | 100.00 |
| 38 | Norit A | 4.5 | 96–98.5 | 1.25 | 100.00 |

EXAMPLE 5

The following series of experiments were conducted in an upflow, continuous tubular reactor (O.D. 1.27 cm, Length 49.5 cm.) having a reaction zone packed with Witco Grade 235 activated carbon 4–10 mesh (14.5 g.). The oxygen and N-phosphonomethylimino diacetic acid were flowed concurrently through the reactor maintained at approximately 95°–100°C. The aqueous acid (4% by wt.) was maintained at 90°C. in a reservoir and the oxygen was preheated to 75°C. Pressure was controlled by means of a pneumatic transmitter-controller downstream of the reactor. A control valve which releases the off gas was employed to achieve the desired flow of oxygen (650 cc./minute).

Liquid samples were withdrawn through a surge tank upstream from the valve. The samples were dehydrated under reduced pressure to yield a solid product which was silylated and analyzed by gas liquid chromatography. The results of these experiments are given in Table V.

TABLE V

| Experiment Number | Pressure Kg/cm$^2$ | Liquid cc./min. | Analysis of Final Solid by GLC (Wt. %) A | B |
|---|---|---|---|---|
| 39 | 3.16 | 3 | 16.8 | 57.6 |
| 40 | 3.16 | 5 | 60.1 | 32.1 |
| 41 | 4.57 | 3 | 14.0 | 47.8 |
| 42 | 4.57 | 5 | 42.0 | 41.2 |
| 43 | 4.57 | 10 | 58.4 | 28.4 |
| 44 | 4.57 | 15 | 63.9 | 24.7 |
| 45 | 5.98 | 3 | 6.5 | 63.5 |
| 46 | 5.98 | 5 | 43.9 | 42.9 |
| 47 | 5.98 | 10 | 59.6 | 25.0 |
| 48 | 5.98 | 15 | 65.3 | 21.0 |
| 49 | 5.98 | 3 | 8.2 | 82.1 |
| 50 | 5.98 | 3 | 16.0 | 79.0 |

A = N-phosphonomethylimino diacetic acid
B = N-phosphonomethyl glycine

EXAMPLE 6

This series of experiments was carried out in a stainless steel autoclave magnetically-stirred with a bottom liquid sampling valve. Oxygen pressure was controlled by means of a back pressure regulator and the flow by a control valve. The oxygen feed was through a dip tube ¼ inch in size with holes drilled in the tube. The catalysts employed in the experimental runs of Table VI were of less than 325 mesh and were employed as slurries. When granular catalysts were employed in Tables VII and VIII, the catalysts were contained in stainless steel baskets attached to the reactor. The baskets were of 100 mesh or 50 mesh stainless steel screen with solid bottoms and affixed to the cooling coils or gas entry tube.

In the experiments, N-phosphonomethylimino diacetic acid (4.0 g.) and 100 ml. of distilled water, were charged into the reactor. The catalyst was charged separately. After closing the reactor, oxygen was continuously flowed through the autoclave to remove air as it was heating up to reaction temperature with stirring at 800 rpm (approximately 30 minutes to reach 95°–102°C.). The reactor pressure was then increased to 3.1 Kg/cm$^2$ and this point was considered reaction time 0. As the reaction proceeded, oxygen was continuously flowed through the reactor at 60 standard cubic centimeters per minute to purge the $CO_2$ from the reactor. When the reaction was terminated, the reactor was cooled and the product drained. Table VI gives the data obtained. Analysis was by NMR after removal of the powdered catalyst. The reaction mixtures employing granular catalysts were not centrifuged but analyzed directly since the granular catalysts were contained in the baskets.

In Tables VI and VII, the time required to convert 95% of the starting N-phosphonomethylimino diacetic acid is given. The analysis was by NMR and showed the presence of greater than 90 - mole (%) of N-phosphonomethyl glycine.

TABLE VI

| Experiment No. | Catalyst | pH | Specific Surface Area m$^2$/g | Time (min.) required for 95% Conversion of Starting Material |
|---|---|---|---|---|
| 51 | None | | NO REACTION | |
| 52 | SXAC Witco Grade* | 7.1 | 1245 | 62 |
| 53 | 256 Witco Grade | 6.2* | 1130 | 81 |
| 54 | 256 Witco Grade* | 9.9 | 1130 | 82 |
| 55 | 235 Baker-Adamson | 6.8* | 1046 | 70 |
| 56 | 1581 | 3.4 | 458 | 70.7% conversion at 180 min. |

*= Washed with deionized water to remove water soluble components.

EXAMPLE 7

In this series of experiments the conditions of reaction are as given in Example 6; however, granular catalysts contained in baskets were employed. For catalyst recycle, the reactor was drained, the reactor and catalyst washed with deionized water and then charged with fresh N-phosphonomethylimino diacetic acid solution. The results of these experiments are given in Table VII.

TABLE VII

| Experiment No. | Basket 1 Catalyst | Mesh | Wt.(g.) | Basket 2 Catalyst Mesh | Wt. (g.) | Time (min.) required for 95% Conversion |
|---|---|---|---|---|---|---|
| 57 | SXAC | 20 × 30 | 1.0 | 20 × 30 | 1.0 | 124 |
| 58 | Grade 235 | 20 × 30 | 1.2 | — | — | — |
| 59 | Grade 235 | recycle of 58 | | 20 × 30 | 1.2 | — |
| 60 | Grade 235 | recycle of 59 | | recycle of 59 | | 150 |
| 61 | Grade 256 | 20 × 30 | 1.0 | 20 × 30 | 1.0 | 140 |
| 62 | SXAC | 20 × 30 | 0.95 | 20 × 30 | 0.95 | 127 |
| 63 | SXAC | 20 × 30 | 1.0 | 20 × 30 | 1.0 | 124 |
| 64 | SXAC | recycle of 63 | | recycle of 63 | | 126 |

In Experiment Number 58, a 57% conversion was obtained after 163 minutes. In Experiment Number 59, the basket holding the catalyst was then moved closer to the gas inlet tube and a 79% conversion to N-phosphonomethyl glycine was obtained after 160 minutes.

EXAMPLE 8

To a glass-lined closed reactor fitted with an agitator was charged 148 parts of N-phosphonomethylimino diacetic acid, 18.5 parts of activated carbon (Norit A, powdered) and 3288.9 parts of water. The agitator-stirrer was started and the mixture heated to 90°C. while maintaining an open vent to the atmosphere. Oxygen gas was then bubbled, via subsurface entry tube, into the mixture while heating was continued to a temperature of 95°C. The reactor vent was then closed and the pressure adjusted to 3.1 Kg/cm$^2$ while maintaining an outlet flow of 2.22 liters/second (1 atmosphere and 26.7°C.). The reactor temperature was maintained at 95°–100°C. and the pressure at 3.1 Kg/cm$^2$ for approximately 1.25 hours. The pressure was then released, the activated carbon removed by filtration. The filtrate was evaporated at atmospheric pressure and then at reduced pressure to yield a white solid. The white solid was washed with 151 parts of water and then dried under vacuum to yield 105.2 parts of a white solid identified as N-phosphonomethyl glycine.

The N-phosphonomethyl glycine produced is useful as a herbicide or plant growth regulant.

What is claimed is:

1. A process for the production of N-phosphonomethyl glycine which comprises contacting an aqueous solution of N-phosphonomethylimino diacetic acid with a molecular oxygen-containing gas at a temperature sufficiently elevated to initiate and sustain reaction and in the presence of a catalyst consisting essentially of activated carbon.

2. A process as claimed in claim 1 wherein the temperature is from 25°C. to 150°C. or higher.

3. A process as claimed in claim 2 wherein the temperature is from 75°C. to 150°C.

4. A process as claimed in claim 1 wherein the pressure of the molecular oxygen-containing gas is from 0.5 Kg/cm$^2$ to 200 Kg/cm$^2$.

5. A process as claimed in claim 4 wherein the pressure is from 1 Kg/cm$^2$ to 7 Kg/cm$^2$.

6. A process as claimed in claim 1 wherein the activated carbon has a surface area of from 100 to 2000 square meters per gram.

7. A process as claimed in claim 6 wherein the activated carbon has a surface area of from 400 to about 1600 square meters per gram.

8. A process as claimed in claim 6 wherein the activated carbon is in powder form.

9. A process as claimed in claim 8 wherein said activated carbon has a particle size smaller than 325 mesh.

10. A process as claimed in claim 6 wherein said activated carbon is in granular form.

11. A process as claimed in claim 10 wherein said activated carbon has a particle size larger than 30 mesh.

12. A process as claimed in claim 11 wherein the particle size of the activated carbon is larger than 20 mesh.

* * * * *